United States Patent
Colabufo (10) Patent No.: US 10,705,099 B2
(45) Date of Patent: Jul. 7, 2020

(54) METHODS AND PROBES FOR DETERMINING THE CONCENTRATION OF COPPER

(71) Applicant: IGEA RESEARCH CORPORATION, Miami, FL (US)

(72) Inventor: Nicola Antonio Colabufo, Bari (IT)

(73) Assignee: IGEA RESEARCH CORPORATION, Miami, FL (US)

( * ) Notice: Subject to any disclaimer, the term of this patent is extended or adjusted under 35 U.S.C. 154(b) by 221 days.

(21) Appl. No.: 15/750,789

(22) PCT Filed: Aug. 6, 2015

(86) PCT No.: PCT/IB2015/055958
§ 371 (c)(1),
(2) Date: Feb. 6, 2018

(87) PCT Pub. No.: WO2017/021759
PCT Pub. Date: Feb. 9, 2017

(65) Prior Publication Data
US 2018/0231574 A1    Aug. 16, 2018

(51) Int. Cl.
*G01N 33/50* (2006.01)
*G01N 33/84* (2006.01)
*G01N 33/68* (2006.01)

(52) U.S. Cl.
CPC ......... *G01N 33/84* (2013.01); *G01N 33/6896* (2013.01); *G01N 2800/2821* (2013.01); *G01N 2800/50* (2013.01)

(58) Field of Classification Search
CPC ............... G01N 33/84; G01N 33/6896; G01N 2800/2821
See application file for complete search history.

(56) References Cited

PUBLICATIONS

Abe, A., et. al., "Sensitive, Direct Colorimetric Assay for Copper in Serum," Clinical Chemistry, vol. 35, No. 4, pp. 552-554, 1989.
International Search Report and Written Opinion issued in PCT Application No. PCT/IB2015/055958 dated Mar. 16, 2016.
Li, Na, et. al., "Fluorescent salicylaldehyde hydrazone as selective chemosensor for ZN in aqueous ethanol: a ratiometric approach," The Journal of Biological and Chemical Luminescence, vol. 25, No. 6, pp. 445-451, Oct. 13, 2009.
Squitti, R., et.al., "Value of Serum Nonceruloplasmin Copper for Prediction of Mild Cognitive Impairment Conversion to Alzheimer Disease," American Neurological Association, vol. 75, No. 4, pp. 574-580, 2014.
Sun, C., et. al., "A New Cu -induced color reaction of a rhodamine derivative N-(3carboxy) acryloyl rhodamine B hydrazide," Science China Chemistry, vol. 54, pp. 1101-1108, 2011.
Kumar, A., et. al., "Highly sensitive and selective naked-eye detection of Cu2+ in aqueous medium by a ninhydrin-quinoxaline derivative" El Sevier, Sensors and Actuators B: Chemical, 176, pp. 420-427, 2013.

*Primary Examiner* — Christopher Adam Hixson
(74) *Attorney, Agent, or Firm* — Arent Fox, LLP (57) ABSTRACT

The present invention relates to new probes and methods for determining the concentration of copper. In particular the present invention refers to a method for determining the concentration of "free" copper in a serum or blood sample with a high degree of sensitivity and accuracy.

13 Claims, 7 Drawing Sheets

METHODS AND PROBES FOR DETERMINING THE CONCENTRATION OF COPPER

CROSS-REFERENCE TO RELATED APPLICATIONS

This application is a National Stage entry of International Application No.: PCT/IB2015/055958, filed Aug. 6, 2015. The disclosure of the priority application is hereby incorporated in its entirety by reference herein.

The present invention relates to new methods and probes for determining the concentration of copper. In particular the present invention refers to a method for determining the concentration of "free" copper in serum or blood samples with a high degree of sensitivity and accuracy.

STATE OF THE PRIOR ART

Transition-metal are crucial for the life processes. In particular, $Cu^{2+}$ is the third in abundance divalent metal ion in human body after $Fe^{2+}$ and $Zn^{2+}$. $Cu^{2+}$ plays an important role in several physiologic processes as a catalytic cofactor for a variety of metallo-enzyme as superoxide dismutase, cytochrome c oxidase, lysyl oxidase and tyrosinase. Moreover $Cu^{2+}$ overloading can be toxic into biological system, and when it exceeds cell needs it could displaces other metal ions involved in physiological pathway. In the last years the involvement of $Cu^{2+}$ in several neurological disorders has been demonstrated. It has been indicated that systemic dyshomeostasis of copper can be one of the pathologic pathways at the basis of Alzheimer Disease. Recent studies have demonstrated that the serum fraction of copper that is not bound to ceruloplasmin (Non-Cpcopper, also known as 'free' copper) increases in a percentage of Alzheimer's Disease patients and mild cognitive impairment subjects. Hence is of primary importance to provide new tools and methods for determining the concentration of copper, in particular in serum or blood samples. Chemo-fluorescent probes chelating selectively $Cu^{2+}$ have been disclosed in the prior art, see for example Sun C et al. *A new Cu2+-induced color reaction of a rhodamine derivative N-(3-carboxy) acryloyl rhodamine B hydrazide*. 2011, 54, 1101-1108, however known probes showed several limitations when used for measuring free copper in serum or blood samples, for example low sensitivity and/or accuracy. Moreover known methods are often expensive and too difficult to perform.

Scope of the present invention is to provide new methods and probes for detecting free copper, in particular for determining the concentration of the free copper in serum or blood samples, which do not entail the drawbacks of the prior art.

SUMMARY OF THE INVENTION

Object of the present invention is an in vitro method for determining the free copper in a liquid sample comprising the following steps:

a) mixing one or more probes chelating $Cu^{2+}$ with said sample, whereby $Cu^{2+}$ chelation causes change of the sample color;

b) determining the concentration of free copper from the change of color of the sample mixed in step a), wherein said probe chelating $Cu^{2+}$ is selected in the group consisting of:
4-(Diethylamino)-2-hydroxy-benzoyl(fluorescein)hydrazine (compound 3);
2,3-Dihydro-5,7-dihydroxy-2-(3-hydroxy-4-methoxyphenyl)chromen-4-(fluorescein)hydrazone (compound 4);
5-(2-Hydroxybenzylideneamino)quinolin-8-ol (compound 6);
Aldehyde,2-hydroxyphenyl-,[2,3-dihydro-5,7-dihydroxy-2-(3-hydroxy-4-methoxyphenyl)chromen-4-ylidene]hydrazine (compound 7);
5-(4-(Diethylamino)-2-hydroxybenzylideneamino)quinolin-8-ol (compound 9);
Aldehyde,2-hydroxyphenyl-[(5-hydroxy-3-methyl-1-phenyl-1H-pyrazol-4yl)-phenyl)-methylidene] hydrazone (compound 10).

A further object of the invention is a kit for the detection of free copper in a serum or blood sample comprising one or more of said probes and one or more finger sticks.

A further object of the invention is the use of one or more of said probes in a kit for the detection of free copper in a sample.

A further object of the invention is an in vitro method for determining the free copper in a sample comprising the following steps.

a) mixing one or more of said probes with said sample;

b) determining the concentration of free copper analyzing the change of color of the sample mixed in step a) by visual inspection or by measuring the absorption spectrum.

A further object of the invention is an in vitro method for determining the concentration of free copper for the diagnosis of Alzheimer's disease in a patient comprising the same steps a), b) and a further step c) of comparing the value determined in step b) with a threshold value (cut-off), wherein a higher concentration of free copper confirms the clinical diagnosis of Alzheimer's disease.

A further object of the invention is an in vitro method for determining the concentration of free copper for the prognosis of Alzheimer's disease in a patient in which the steps a) and b) of the method are repeated on said samples collected from said patient at subsequent time-points and the progression in time of the concentration of free copper in these samples is evaluated.

A further object of the invention is an in vitro method for determining the concentration of free copper for the evaluation of the predisposition to conversion from a state of mild cognitive impairment (MCI) to Alzheimer's disease in a patient suffering from mild cognitive impairment comprising the same steps a) and b) and a further step c) of comparing the value determined in step b) with a threshold value (cut-off), wherein a higher concentration of free copper points out the conversion from mild cognitive impairment to Alzheimer's disease.

In a specific embodiment of the invention, said sample is a diluted or undiluted blood or serum sample obtained by said patient.

A further object of the invention are the following probes and the process for their synthesis:
4-(Diethylamino)-2-hydroxy-benzoyl(fluorescein)hydrazine;
2,3-Dihydro-5,7-dihydroxy-2-(3-hydroxy-4-methoxyphenyl)chromen-4-(fluorescein)hydrazone;
5-(2-Hydroxybenzylideneamino)quinolin-8-ol;
Aldehyde,2-hydroxyphenyl-,[2,3-dihydro-5,7-dihydroxy-2-(3-hydroxy-4-methoxyphenyl)chromen-4-ylidene]hydrazine;
5-(4-(Diethylamino)-2-hydroxybenzylideneamino)quinolin-8-ol; Aldehyde,2-hydroxyphenyl-[(5-hydroxy-3-methyl-1-phenyl-1H-pyrazol-4yl)-phenyl)-methylidene] hydrazone.

The probes of the present invention entails several advantages compared to the probes of the state of the art. The probes are novel colorimetric naked-eye chemosensor for a selective and simple-to-use recognition of $Cu^{2+}$ in serum of patients. In particular the probes can be easily applied in a method wherein a fingerstick is used to collect a drop of blood into an appropriate probe solution. The probes are a selective $Cu^{2+}$ chelating agents and in presence of this ion a change in color is observed: from the initial color of the free probe to the typical color of the complex probe-$Cu^{2+}$.

Advantageously three of these probes, i.e. 4-(Diethylamino)-2-hydroxy-benzoyl(fluorescein)hydrazine, 2,3-Dihydro-5,7-dihydroxy-2-(3-hydroxy-4-methoxyphenyl)chromen-4-(fluorescein)hydrazone and 5-(2-Hydroxybenzylideneamino)quinolin-8-ol, visualizes $Cu^{2+}$ at concentration below 2 microM, in particular at 1.9 microM concentration. Each of these three specific probes, in appropriate conditions, change in color at $Cu^{2+}$ concentration >2 microM. If the test is positive a change in color of all these three probes solutions is observed.

BRIEF DESCRIPTION OF THE FIGURES

FIG. 4 is a schematic view of the method for determining free copper in a blood sample according to one embodiment of the present invention: FIG. 4A. A drop of blood is collected in a vial with THF. FIG. 4B. Vial is upside down and blood is filtered. FIG. 4C. Blood is added to vial B with different probes solutions. Color change is observed.

DETAILED DESCRIPTION OF THE INVENTION

As previously indicated, the present invention relates to a probe chelating $Cu^{2+}$ selected in the group consisting of:
4-(Diethylamino)-2-hydroxy-benzoyl(fluorescein)hydrazine (i.e. compound 3);
2,3-Dihydro-5,7-dihydroxy-2-(3-hydroxy-4-methoxyphenyl)chromen-4-(fluorescein)hydrazone (i.e. compound 4);
5-(2-Hydroxybenzylideneamino)quinolin-8-ol (i.e. compound 6);
Aldehyde,2-hydroxyphenyl-,[2,3-dihydro-5,7-dihydroxy-2-(3-hydroxy-4-methoxyphenyl)chromen-4-ylidene]hydrazine (i. e. compound 7);
5-(4-(Diethylamino)-2-hydroxybenzylideneamino)quinolin-8-ol (i.e. compound 9);
Aldehyde,2-hydroxyphenyl-[(5-hydroxy-3-methyl-1-phenyl-1H-pyrazol-4yl)-phenyl)-methylidene] hydrazone (i.e. compound 10).

These probes are part of a kit for the detection of free copper in a biological sample, the kit further comprising one or more aliquots of said probes and one or more finger sticks. The sample is selected from a serum or a blood sample either in diluted or undiluted form. The kit may further comprise one or more vials and/or means for filtering, such as filter papers, and/or solvents suitable for dissolving said probes such as $CHCl_3$, EtOH, THF, or their mixture. In one embodiment the kit further comprises one or more aliquots of controls having a known titer of copper; these controls may be optionally used to prepare a calibration curve.

A further object of the present invention is an in vitro method for determining the free copper in a sample comprising a step a) of mixing one or more of said probes, preferably already in a solution, with said liquid sample and a step b) of determining the concentration of free copper. The chelation of free copper by the probe causes a change in color of the solution. Compound 3 changes from light green to yellow, Compound 4 changes from blank to light red, Compound 6 changes from light yellow to dark yellow, Compound 7 changes from yellow to orange, Compound 9 changes from blank to dark yellow, Compound 10 changes from light yellow to dark yellow.

Thus the concentration of free copper may be determined from the change of color of the sample mixed in step a). The change in color may be analyzed, for example, either by visual inspection or by measuring the absorption spectrum. The entire method is therefore extremely quick, cheap and easily to perform.

In one embodiment the sample may be a serum or a blood sample, advantageously before mixing said sample with said probes the sample may be diluted with suitable buffers such phosphate buffers and/or filtered for example using a filter paper.

Figure 4:
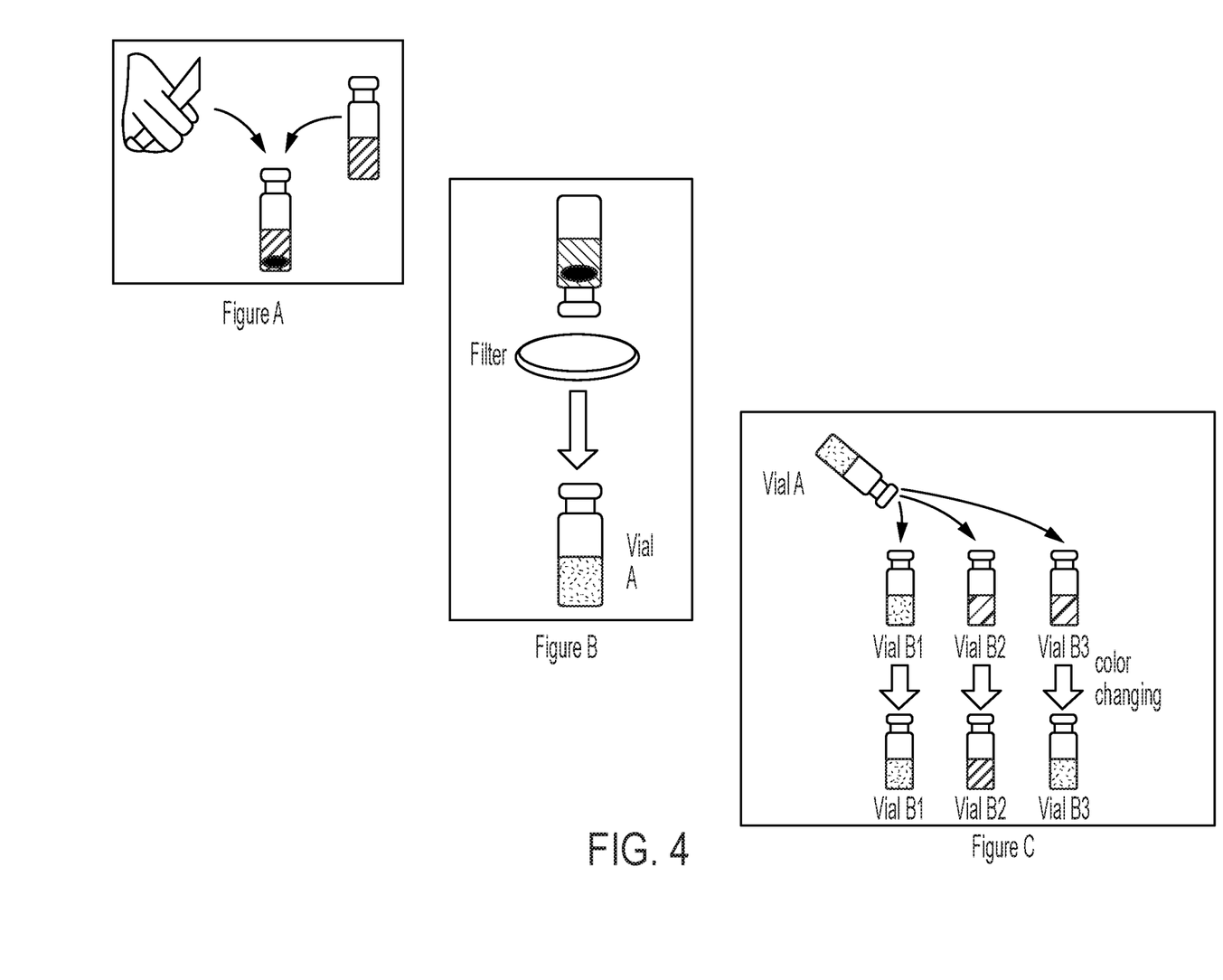

In one embodiment of the method, schematically depicted in FIG. 4, a drop of blood obtained using a fingerstick is collected in a vial with a suitable solution, as for example THF. The vial is then upside down and blood is filtered using for example a filter paper. Filtered blood is added to a second vial with said probes solution, preferably NaOH is then added to the solution. Color change may be observed depending from the concentration of $Cu^{2+}$ in the sample.

As previously reported in patients affected by Alzheimer's Disease, serum copper not bound to ceruloplasmin ('free' copper) appears elevated and the increase, though slight, is normally sufficient to distinguish Alzheimer's Disease patients from healthy elderly subjects (also in the early stages of the disease).

Hence the in vitro method of the present invention intended for the diagnosis of Alzheimer's disease in a patient suspected of having Alzheimer's Disease comprises a further step c) of comparing the value determined in step b) with a threshold value (cut-off), wherein a higher concentration of free copper confirms the clinical diagnosis of Alzheimer's disease.

By the expression "in vitro method for the diagnosis of Alzheimer's disease" it is meant a method for confirming the clinical diagnosis of Alzheimer's Disease in a patient suspected of having Alzheimer's Disease.

Evidently, if before being mixing with the probe the serum or blood sample has been diluted according to a certain dilution factor, in step c), of comparing with the threshold value, the free copper concentration determined in step b) will have to be multiplied by the dilution factor.

The threshold value (cut-off) of copper may be determined for example by means of ROC (Receiver Operating Characteristic) curves obtained by processing the concentrations of a set of samples (statistically significant) of healthy individuals and individuals with Alzheimer's disease. Through such processing, threshold values were obtained between 0.5 and 50 μm, preferably between 2 and 3 μm.

Preferably said diagnosis method will be used as a confirming test for a clinical diagnosis of Alzheimer's disease in a patient suspected of having Alzheimer's Disease with a 'copper phenotype dysfunction'.

As shown by Squitti et al., *Neurology* (2009) to monitor the prognosis of Alzheimer's Disease in a patient as well as to predict the conversion from mild cognitive impairment (Mild cognitive Impairment) to Alzheimer's disease it is important to determine the concentration of free copper in the serum of said patient (FIG. 5).

The clinical condition of Mild Cognitive Impairment (MCI) is characterized by memory impairments, verifiable via objective measures, not yet granting the definition of dementia. The importance of an accurate diagnosis lies in the fact that, despite the mildness of the condition, MIC is normally considered as a precursor of Alzheimer's disease. This is due to the high statistical rate of progression from Mild cognitive impairment to Alzheimer's Disease.

Hence in one embodiment, the method of the present invention is used for predicting the conversion from a state of mild cognitive impairment (MCI) to Alzheimer's disease in a patient suffering from mild cognitive impairment comprising a step c) of comparing the value determined in step b) with a threshold value (cut-off), in which a higher concentration of copper indicates the conversion from MCI to Alzheimer's disease. This threshold value is for example between 0.5 and 3 μM, preferably 2 μM. Steps a) and b) of said prediction method may be performed according to any embodiments of the above-disclosed steps a) and b).

A further embodiment of the present invention is an in vitro method for the prognosis of Alzheimer's disease in a patient wherein the steps a) and b) of the method according to any embodiments of the above-disclosed steps a) and b) are carried out on more samples of said patient collected in different moments and the quantification of data obtained from each sample are compared one to the other, thus constructing a progression in time of the concentration of free copper in the serum samples of said patient.

A further embodiment of the present invention is a process for the synthesis of the probes disclosed above.

4-(Diethyl amino)-2-hydroxy-benzoyl(fluorescein)hydrazine is prepared by condensation of 4-diethylamino-salicyaldehyde with fluorescein hydrazide. Fluorescein hydrazide may be prepared by reaction of fluorescein with hydrazine hydrate.

2,3-Dihydro-5,7-dihydroxy-2-(3-hydroxy-4-methoxyphenyl)chromen-4-(fluorescein)hydrazone is prepared by condensation of compound 2 with hesperetin.

5-(2-Hydroxybenzylideneamino)quinolin-8-ol is synthesized by reaction of 5-amino-8-hydroxyquinoline 5 with salicylaldehyde.

Aldehyde,2-hydroxyphenyl-,[2,3-dihydro-5,7-dihydroxy-2-(3-hydroxy-4-methoxyphenyl)chromen-4-ylidene]hydrazine is prepared by condensation of amine 5 with 4-diethylamino-salicylaldehyde (Scheme 2).

5-(4-(Diethylamino)-2-hydroxybenzylideneamino)quinolin-8-ol; has been synthesized reacting amine 8, prepared as already reported in Kumar et al. *Sensor and Actuators B*, 2013, 176, 420-427, with 1-phenyl-3-methyl-4-benzoyl-5-pyrazolone.

5-(4-(Diethylamino)-2-hydroxybenzylideneamino)quinolin-8-ol is prepared by condensation of amine 8 with hesperetin (Scheme 3).

Examples aimed at illustrating some embodiments of the present invention are reported here below; in no way such examples are to be construed as a limitation of the present description and of the subsequent claims.

EXAMPLES

Example 1 (Materials and Instruments)

Column chromatography was performed with Merck silica gel 60 Å (63-200 m) as the stationary phase. ESI-MS analyses were performed on an Agilent 1100 LC/MSD trap system VL (Santa Clara, USA), only significant m/z peaks, with their percentage of relative intensity in parentheses, are reported. $^1$H NMR spectra were recorded in d6-DMSO at 500 μMHz with an Avance 500 μMHz spectrometer (Bruker, Billerica, USA). Commercially available chemicals were purchased from Sigma-Aldrich. The IR spectra were recorded on Perkin Elmer Spectrum One FT-IR Spectrometer, solids were recorded as KBr pallets.

Example 2 (Chemistry Synthesis)

Compounds 3, 4, 6, 7, 9, 10 were synthesized as displayed in Scheme 1, 2 and 3. Synthesis of compound CARB2 have been reported previously, and spectral data of this compounds were identical to those previously described in Sun C et al. *A new Cu 2+-induced color reaction of a rhodamine derivative N-(3-carboxy)acryloyl rhodamine B hydrazide*. 2011, 54, 1101-1108.

CARB2

Compound 3 has been synthesized by condensation of 4-diethylamino-salicyaldehyde with fluorescein hydrazide 2 previously prepared by reaction of fluorescein 1 with hydrazine hydrate. Compound 4 was prepared by condensation of compound 2 with hesperetin (Scheme 1). Compound 6 has been synthesized by reaction of 5-amino-8-hydroxyquinoline 5 with salicylaldehyde. Compound 7 has been prepared by condensation of amine 5 with 4-diethylamino-salicylaldehyde (Scheme 2). Compound 9 has been synthesized reacting amine 8, prepared as already reported in Kumar et al. *Sensor and Actuators B*, 2013, 176, 420-427, with 1-phenyl-3-methyl-4-benzoyl-5-pyrazolone. Compound 10 has been prepared by condensation of amine 8 with hesperetin (Scheme 3).

Scheme 1

Scheme 2

Scheme 3

10

Example 3 (Organic Synthesis)

4-(Diethylamino)-2-hydroxy-benzoyl(fluorescein) hydrazone (compound 3)

A solution of 4-diethylamino-salicyaldehyde (750 mg, 3.88 mmol) and fluorescein hydrazide 2 (300 mg, 0.86 mmol) in ethanol (20 ml) was refluxed for 6 h with stirring during which time which the mixture color slowly changes to yellow to light orange. The solvent was evaporated and was purified on silica gel column chromatography ($CHCl_3$/MeOH 19:1 v/v) and recrystallized from $CHCl_3$ to obtain 100 mg of 3 as yellow solid (15%). $ESI^+$/MS m/z: 544 $[M+Na]^+$, $ESI^+$/MS/MS m/z: 515 (15). $^1H$ NMR (500 μMHz, d6-DMSO) δ: 10.42 (bs, 1H, OH), 9.9 (bs, 1H, OH), 8.9 (s, 1H), 7.88-7.87 (s, 1H), 7.59-7.57 (m, 2H), 7.11 (d, 1H, J=2 Hz), 7.01 (d, 1H, J=9 Hz), 6.61 (d, 2H, J=2 Hz), 6.49-6.44 (m, 4H), 6.18-6.16 (m, 1H), 5.95 (d, 1H, J=4 Hz), 3.31-3.26 (m, 4H), 2.49 (t, 6H). IR ($cm^{-1}$, KBr film): 3353 (—OH), 2969, 1667, 1645, 1240.

2,3-Dihydro-5,7-dihydroxy-2-(3-hydroxy-4-methoxyphenyl)chromen-4-(fluorescein)hydrazone (compound 4)

A solution of hesperetin (590 mg, 1.96 mmol) and fluorescein hydrazide 2 (600 mg, 1.73 mmol) in methanol (30 ml) and $H_2SO_4$ (0.5 mL) was stirred at 600 for 24 h. The solvent was evaporated and the residue was purified on silica gel column chromatography ($CHCl_3$/MeOH 19:1 v/v) and recrystallized from $CHCl_3$ to obtain 80 mg of 4 as yellow solid (8%). $ESI^-$/MS m/z: 629 $[M]^-$, $ESI^-$/MS/MS m/z: 611 (46), 585 (100). $^1H$ NMR (500 μMHz, d6-DMSO) δ: 11.42 (bs, 1H, OH), 10.21 (bs, 1H, OH), 7.8 (d, 1H, J=5 Hz), 7.61-7.59 (m, 2H), 7.15 (d, 1H, J=5 Hz), 6.69-6.25 (m, 8H), 6.18-6.16 (m, 1H), 5.82 (s, 1H), 5.81 (s, 1H), 4.91-4.36 (m, 4H), 3.73 (s, 3H, $CH_3$), 2.72-2.63 (m, 4H). IR ($cm^{-1}$, KBr film): 3365 (—OH), 2933, 1634, 1610, 1261.

5-(2-Hydroxybenzylideneamino)quinolin-8-ol (compound 6)

A solution of 5-amino-8-hydroxyquinoline 5 (500 mg, 2.14 mmol), salicylaldehyde (524 mg, 4.28 mmol) and a pinch of p-toluene sulfonic acid in toluene (10 ml) was refluxed for 18 h with stirring. The solvent was evaporated and was purified on silica gel column chromatography ($CH_2Cl_2$ v/v) to obtain 180 mg of 6 as dark solid (15%). $ESI^-$/MS m/z: 263 $[M]^-$, $ESI^-$/MS/MS m/z: 236 (80), 169 (100), 144 (34). $^1H$ NMR (500 μMHz, d6-DMSO) δ: 13.0 (bs, 1H, OH), 10.04 (bs, 1H, OH), 9.3-9.0 (m, 3H), 8.55 (s, 1H), 7.72-7.43 (m, 4H), 7.16-7.0 (m, 2H). IR ($cm^{-1}$, KBr film): 3453 (—OH), 1609, 1458.

5-(4-(Diethylamino)-2-hydroxybenzylideneamino)quinolin-8-ol (compound 7)

A solution of 5-amino-8-hydroxyquinoline 5 (500 mg, 2.14 mmol), 4-diethylamino-salicylaldehyde (830 mg, 4.44 mmol) $H_2SO_4$ (0.2 mL) in $CH_3OH$ (30 ml) was refluxed for 1 h with stirring. The solvent was evaporated and the solid was recrystallized by $CH_2Cl_2$ to obtain 200 mg of 7 as red solid (15%). $ESI^+$/MS m/z: 336 $[M]^+$, $ESI^+$/MS/MS m/z: 319 (100), 265 (45), 166 (89). IR ($cm^{-1}$, KBr film): 3200 (—OH), 1591, 1411.

Aldehyde,2-hydroxyphenyl-[(5-hydroxy-3-methyl-1-phenyl-1H-pyrazol-4yl)-phenyl)-methylidene]hydrazone (compound 9)

A solution of amine 8 (300 mg, 2.22 mmol), 1-phenyl-3-methyl-4-benzoyl-5-pyrazolone (1.2 g, 3.5 mmol) and a pinch of p-toluene sulfonic acid in toluene (10 ml) was refluxed for 15 h with stirring. The solvent was evaporated and was purified on silica gel column chromatography ($CH_2Cl_2$ v/v) to obtain 250 mg of 9 as yellow solid (17%). $ESI^+$/MS m/z: 419 $[M+Na]^+$, $ESI^+$/MS/MS m/z: 299 (80), 197 (26). $^1H$ NMR (500 μMHz, d6-DMSO) δ: 9.9 (bs, 1H, OH), 9.7 (bs, 1H, OH), 8.7 (1H, s), 8.23-8.10 (m, 1H), 8.09-7.95 (m, 2H), 7.93-7.75 (m, 1H), 7.75-7.55 (m, 5H), 7.51-7.41 (m, 3H), 7.20-7-07 (m, 2H), 2.4 (s, 3H). IR ($cm^{-1}$, KBr film): 3064 (—OH), 1620, 1574, 1488.

Aldehyde,2-hydroxyphenyl-,[2,3-dihydro-5,7-dihydroxy-2-(3-hydroxy-4-methoxyphenyl)chromen-4-ylidene]hydrazine (compound 10)

A solution of amine 8 (270 mg, 1.9 mmol), hesperetin (300 mg, 0.99 mmol) $H_2SO_4$ (0.2 mL) in $CH_3OH$ (30 ml) was refluxed for 1 h with stirring. The precipitated was filtered and the solid was collected to obtain 10 as yellow solid (44%). ESI/MS m/z: 419 $[M]^-$, ESI/MS/MS m/z: 375 (100), 333 (38). IR ($cm^{-1}$, KBr film): 3243 (—OH), 2640, 1620.

UV-Visible Studies

Figure 1A:
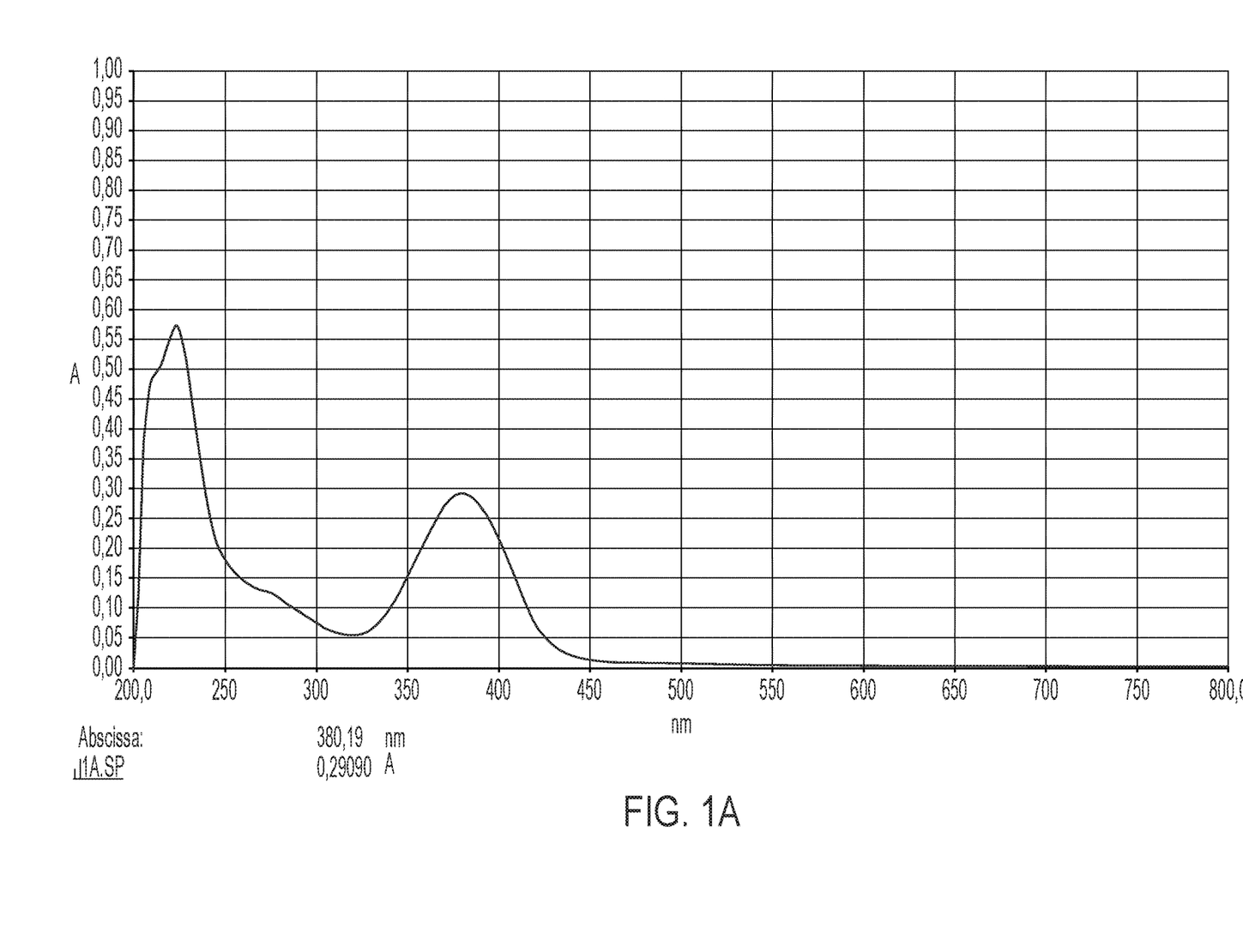
FIG. 1A shows the absorption spectrum of compound 3, i.e. -4-(Diethylamino)-2-hydroxy-benzoyl(fluorescein)hydrazine).
Figure 1B:
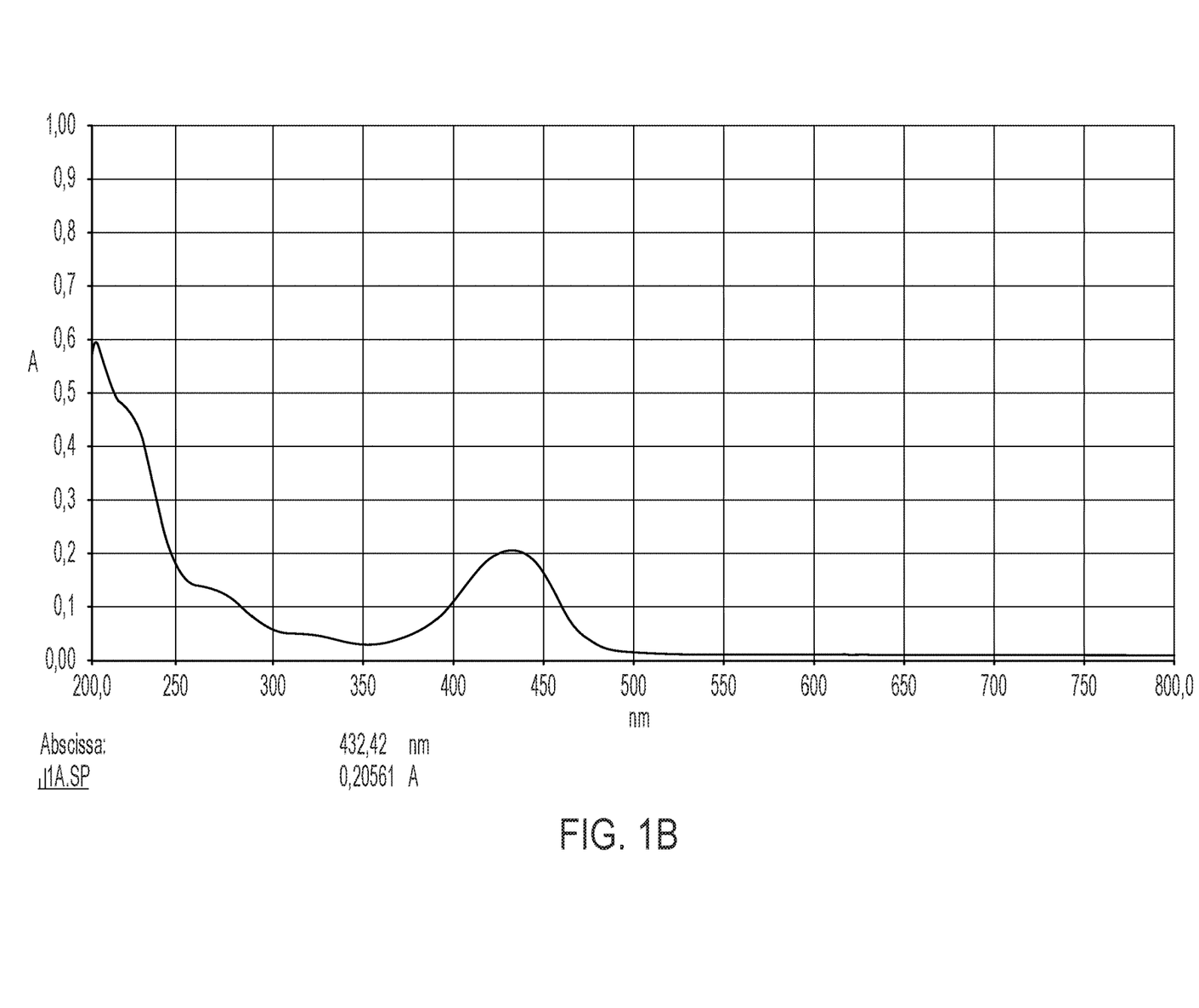
FIG. 1B shows the absorption spectrum of compound 3, in the presence of $Cu^{2+}$.
Figure 2A:
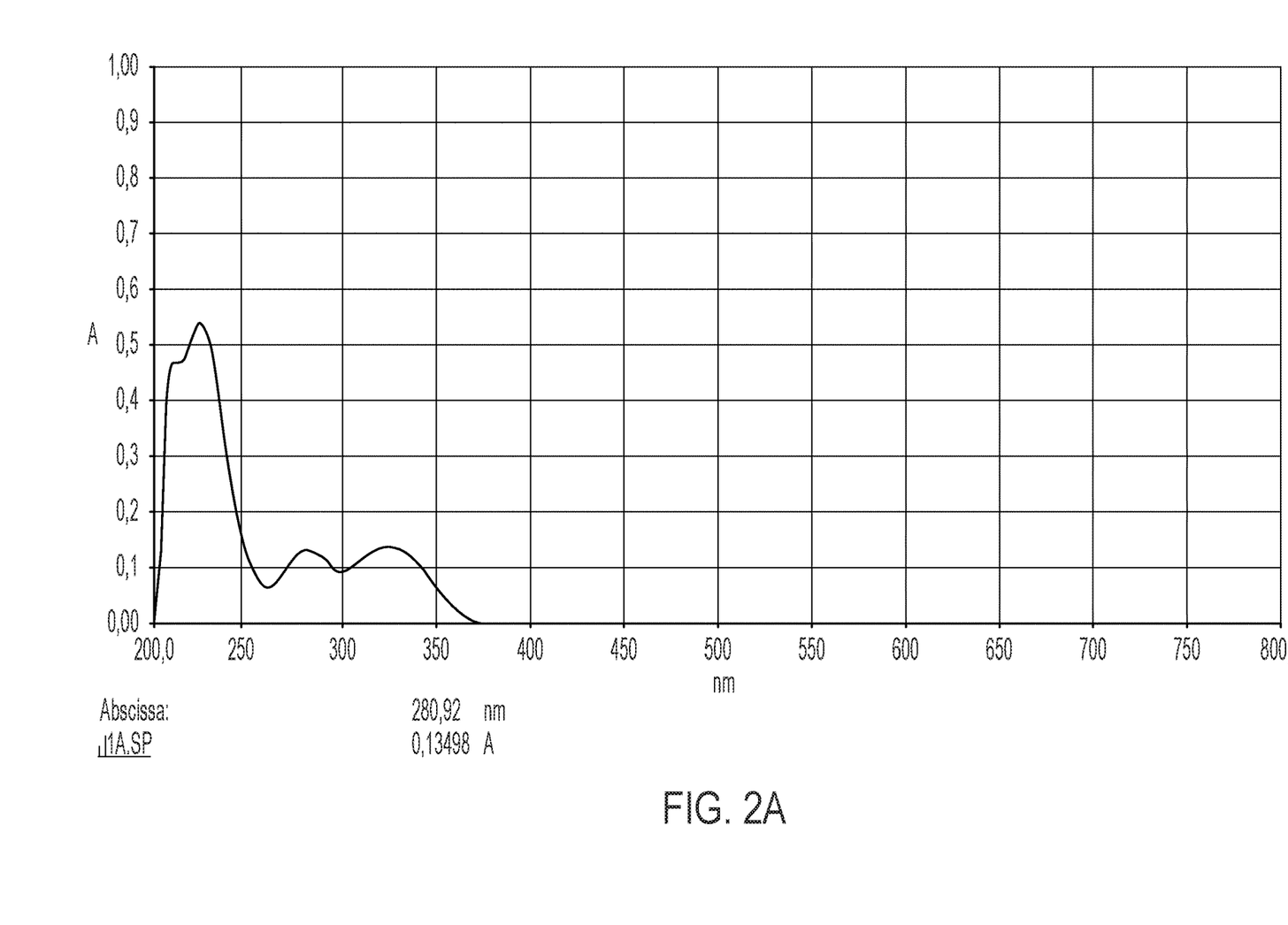
FIG. 2A shows the absorption spectrum of compound 4, i.e -2,3-Dihydro-5,7-dihydroxy-2-(3-hydroxy-4-methoxyphenyl)chromen-4-(fluorescein)hydrazone.
Figure 2B:
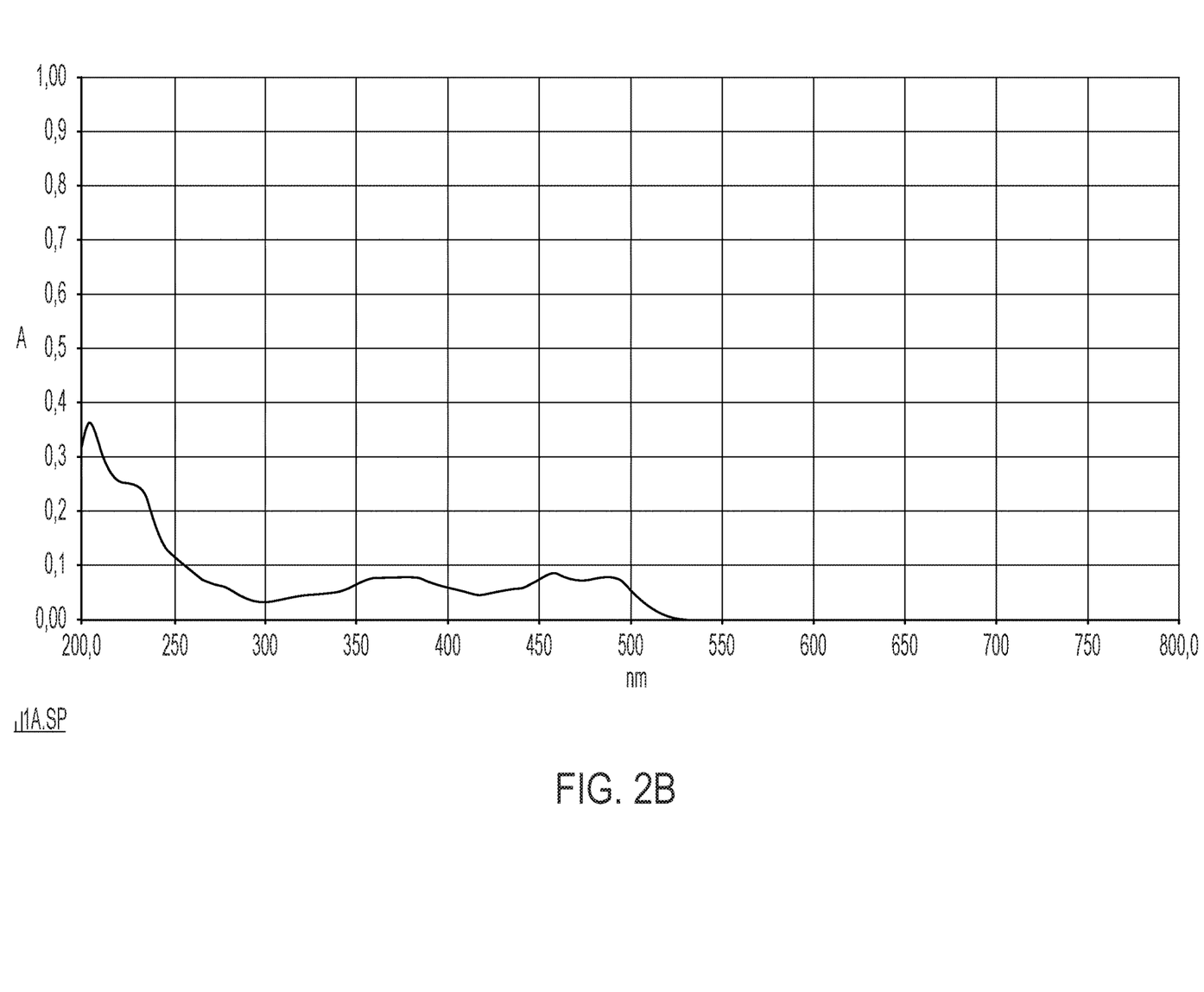
FIG. 2B shows the absorption spectrum of compound 4 in presence of $Cu^{2+}$.
Figure 3A:
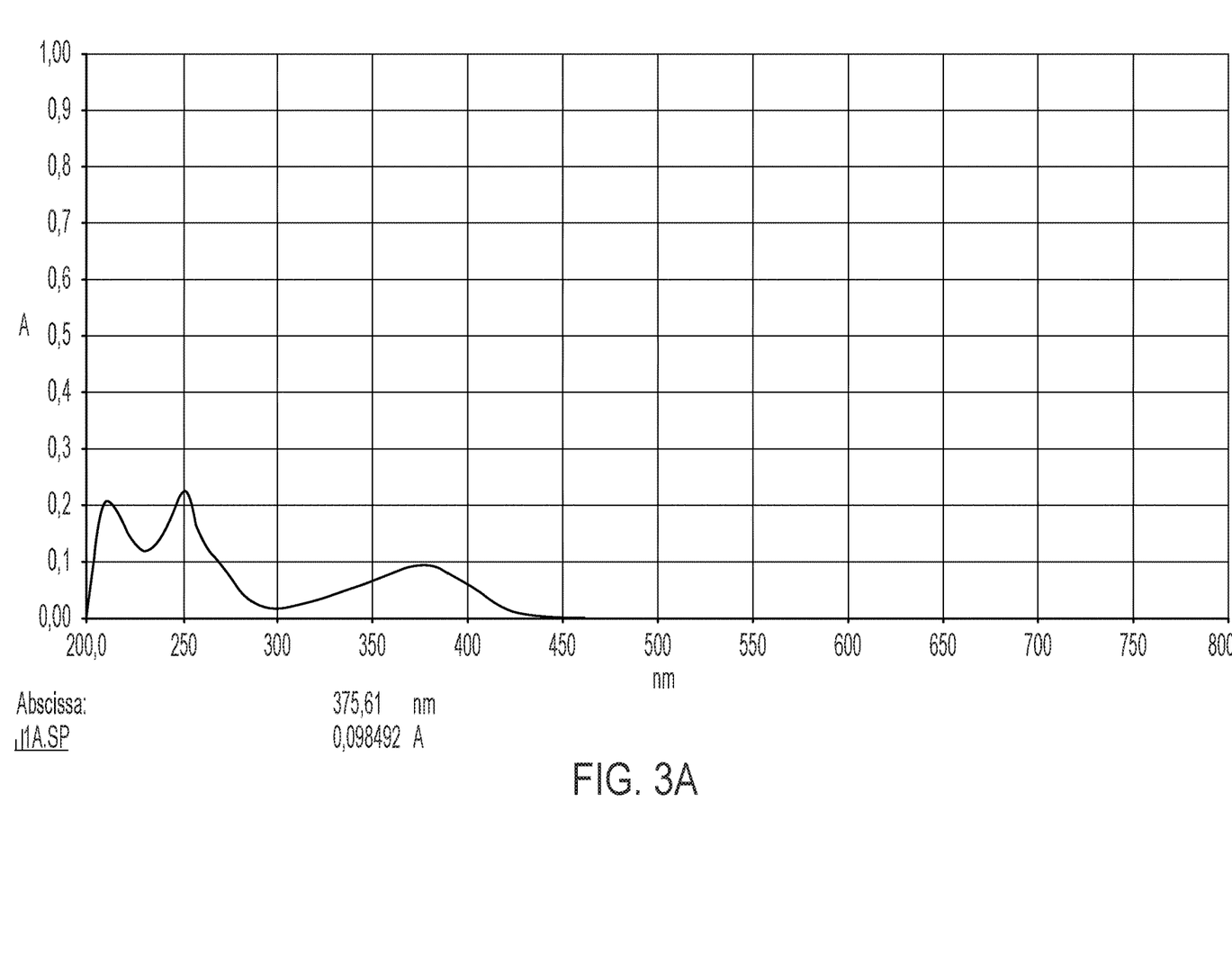
FIG. 3A shows the absorption spectrum of compound 6, i.e -5-(2-Hydroxybenzylideneamino)quinolin-8-ol.
Figure 3B:
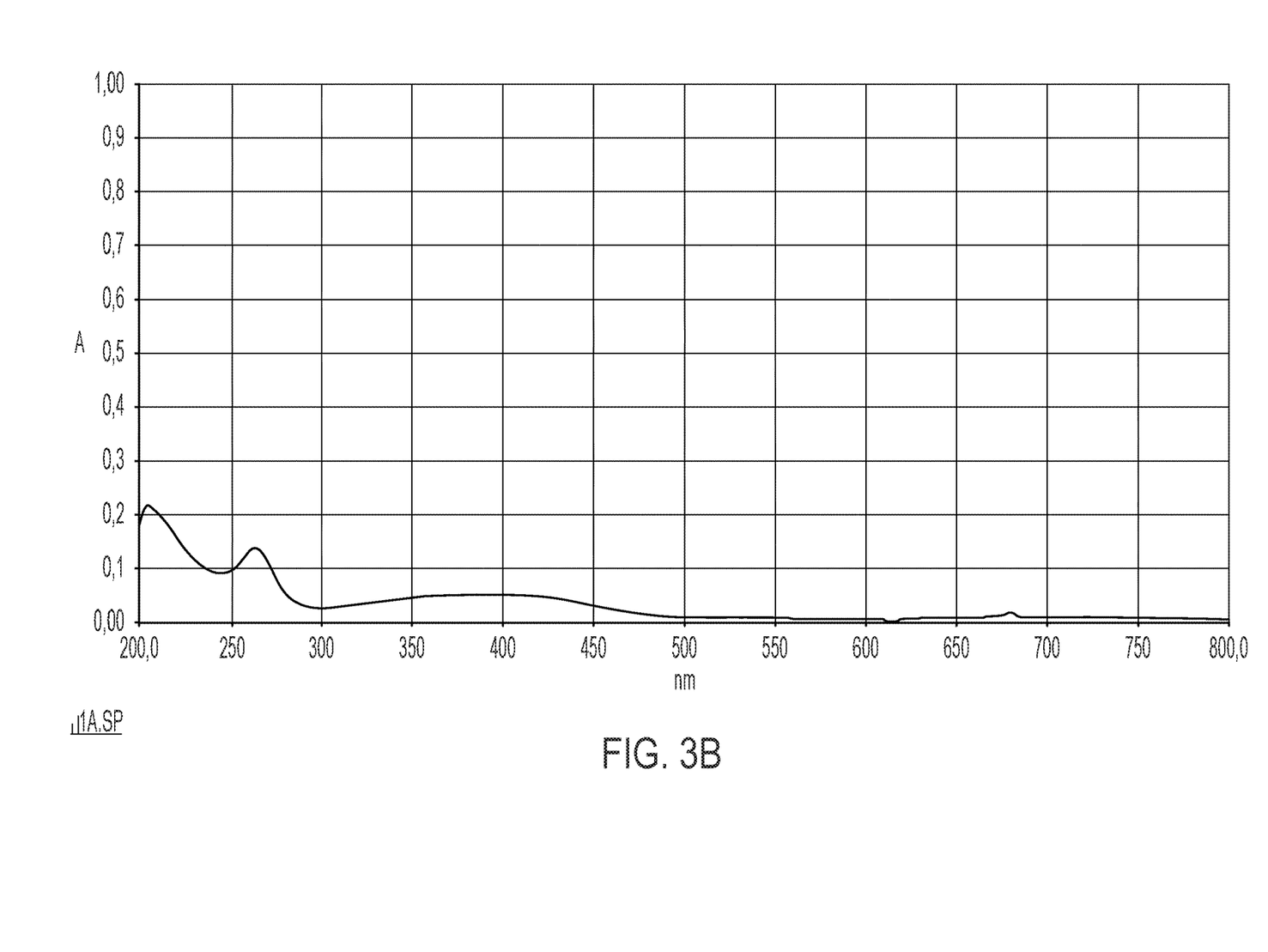
FIG. 3B shows the absorption spectrum of compound 6 in presence of $Cu^{2+}$.

All spectroscopic measurements of compounds 3, 4, 6 (FIG. 1A) were performed in its $1\times10^{-5}$ μM EtOH solution. FIG. 1 shows the changes in the absorption spectrum of compounds upon addition of 500 μl $CuCl_2$ 200 μM to 500 μl of probe solution.

Example 4 Visual Detection of $Cu^{2+}$

A drop of blood (3 μl) is diluted in 50 μl of THF, filtered with Whatmann Filter Papers (1—Cat No 1001-150) and collected in vial A. The probe's solution is prepared in vial B in appropriate conditions for each probe:
  Compound 3: 50 μl of probe $1\times10^{-4}$ M dissolved in $CHCl_3$;
  Compound 4: 50 μl of probe $1\times10^{-3}$ M dissolved in EtOH;
  Compound 6: 50 μl of probe $1\times10^{-4}$ M dissolved in THF;
  Compound 7: 50 μl of probe $1\times10^{-3}$ M] dissolved in $CH_3CN$;
  Compound 9: 50 μl of probe $1\times10^{-5}$ M dissolved in EtOH;
  Compound 10: 50 μl of probe $1\times10^{-2}$ M dissolved in EtOH.

Solution of vial A is added to vial B by pipetting from the bottom of the vial, then NaOH 2.5 μM (2.5 μM) is added. The color change was observed in few minutes as a sensitive naked-eye indicator for $Cu^{2+}$ concentration.

Limits and color changes are displayed below:
  Compound 3: from light green to yellow visible from $Cu^{2+}$[2 μM];
  Compound 4: from blank to light red visible from $Cu^{2+}$[2 μM];
  Compound 6: from light yellow to dark yellow visible from $Cu^{2+}$[2 μM];
  Compound 7: from yellow to orange visible from $Cu^{2+}$[10 μM];
  Compound 9: from blank to dark yellow visible from $Cu^{2+}$[10 μM];
  Compound 10: from light yellow to dark yellow visible from $Cu^{2+}$[2 μM]

Compound CARB2 was used as internal standard. In a vial, 96 μL of 0.2 mol/L Palitzsch's buffer solution (pH 7.0), 9.3 μL of THF, and 2.7 μL of CARB2 solution $2\times10^{-2}$ μM were mixed, followed by addition of an appropriate volume of $Cu^{2+}$ sample solution. The final volume was adjusted to 120 μL with water, and the reaction solution was thoroughly mixed. The color change appear immediately increasing directly with the $Cu^{2+}$ concentration switching from blank to dark purple with naked eye limit of 4 μM.

The invention claimed is:

1. A method for determining free copper in a liquid sample, comprising
  mixing one or more $Cu^{2+}$ chelating probes with said sample; and
  measuring a color change in the sample to determine the concentration of free copper;
  wherein said probe comprises:
    4-(Diethylamino)-2-hydroxy-benzoyl(fluorescein)hydrazine;
    2,3-Dihydro-5,7-dihydroxy-2-(3-hydroxy-4-methoxyphenyl)chromen-4-(fluorescein)hydrazone;
    5-(2-Hydroxybenzylideneamino)quinolin-8-ol;
    Aldehyde,2-hydroxyphenyl-, [2,3-dihydro-5,7-dihydroxy-2-(3-hydroxy-4-methoxyphenyl)chromen-4-ylidene]hydrazine;
    5-(4-(Diethylamino)-2-hydroxybenzylideneamino)quinolin-8-ol;
    Aldehyde,2-hydroxyphenyl-[(5-hydroxy-3-methyl-1-phenyl-1H-pyrazol-4yl)-phenyl)-methylidene] hydrazine; or
    combinations thereof.

2. The method according to claim 1, wherein said probe comprises:
    4-(Diethylamino)-2-hydroxy-benzoyl(fluorescein)hydrazine;
    2,3-Dihydro-5,7-dihydroxy-2-(3-hydroxy-4-methoxyphenyl)chromen-4-(fluorescein)hydrazone;
    5-(2-Hydroxybenzylideneamino)quinolin-8-ol; or
    combinations thereof.

3. The method according to claim 1, wherein the measuring of the color change is performed by visual inspection or by measuring an absorption spectrum.

4. The method according to claim 1, wherein said sample is serum or a blood sample.

5. The method according to claim 1, further comprising diluting and/or filtering said sample before mixing said sample with said one or more probes.

6. The method according to claim 1, wherein a measured color change in said sample exceeding a threshold value (cut-off) is indicative of a clinical diagnosis of Alzheimer's disease.

7. The method according to claim 6, wherein said threshold value is between 2 and 50 μM.

8. The method according to claim 1, wherein a measured color change in said sample exceeding a threshold value (cut-off) is indicative of a predisposition to Alzheimer's disease in a patient suffering from mild cognitive impairment (MCI).

9. The method according to claim 8, wherein said threshold value is between 2 and 3 μM.

10. The method according to claim 6, wherein the measuring is repeated at subsequent time-points and a progression in time of a value of the measured color change is evaluated.

11. A method of diagnosing a predisposition to Alzheimer's disease in a patient suffering from mild cognitive impairment (MCI) comprising:
    mixing one or more Cu2+ chelating probes with an extracted sample from the patient; and
    measuring a color change in the sample,
    wherein the one or more probes comprises
    4-(Diethylamino)-2-hydroxy-benzoyl(fluorescein)hydrazine;
    2,3-Dihydro-5,7-dihydroxy-2-(3-hydroxy-4-methoxyphenyl)chromen-4-(fluorescein)hydrazone;
    5-(2-Hydroxybenzylideneamino)quinolin-8-ol;
    Aldehyde,2-hydroxyphenyl-,[2,3-dihydro-5,7-dihydroxy-2-(3-hydroxy-4-methoxyphenyl)chromen-4-ylidene] hydrazine;
    5-(4-(Diethylamino)-2-hydroxybenzylideneamino)quinolin-8-ol;
    Aldehyde,2-hydroxyphenyl-[(5-hydroxy-3-methyl-1-phenyl-1H-pyrazol-4yl)-phenyl)-methylidene]hydrazine; or any combination thereof; and
    wherein a measured color change in said sample exceeding a threshold value (cut-off) is indicative of the predisposition to Alzheimer's disease in the patient.

12. The method according to claim 11, wherein said sample is serum or a blood sample.

13. The method according to claim 11, wherein said threshold value is between 2 and 3 μM.

* * * * *